(12) United States Patent
Baid

(10) Patent No.: US 9,440,053 B2
(45) Date of Patent: Sep. 13, 2016

(54) NEEDLE TIP PROTECTOR ASSEMBLY FOR SAFETY IV CATHETER ASSEMBLY

(75) Inventor: Rishi Baid, New Delhi (IN)

(73) Assignee: POLY MEDICURE LIMITED, Faridabad (IN)

( * ) Notice: Subject to any disclaimer, the term of this patent is extended or adjusted under 35 U.S.C. 154(b) by 73 days.

(21) Appl. No.: 14/235,193

(22) PCT Filed: Jul. 26, 2012

(86) PCT No.: PCT/IB2012/053819
§ 371 (c)(1),
(2), (4) Date: Jan. 27, 2014

(87) PCT Pub. No.: WO2013/014638
PCT Pub. Date: Jan. 31, 2013

(65) Prior Publication Data
US 2014/0180212 A1 Jun. 26, 2014

(30) Foreign Application Priority Data
Jul. 26, 2011 (IN) .............................. 2108/DEL/2011

(51) Int. Cl.
*A61M 25/06* (2006.01)
*A61M 5/32* (2006.01)

(52) U.S. Cl.
CPC ..... *A61M 25/0631* (2013.01); *A61M 25/0618* (2013.01); *A61M 5/3273* (2013.01); *A61M 25/0606* (2013.01); *A61M 2005/325* (2013.01)

(58) Field of Classification Search
CPC .................... A61M 25/0606; A61M 25/0618; A61M 25/0612
USPC ............ 604/164.01, 164.06, 164.07, 164.08, 604/165.01, 263, 272
See application file for complete search history.

(56) References Cited

U.S. PATENT DOCUMENTS 5,279,591 A     1/1994  Simon
6,468,248 B1 * 10/2002  Gibbs ...................... 604/164.01
(Continued)

FOREIGN PATENT DOCUMENTS

WO         03011381 A1    2/2003
WO      2005042073 A1    5/2005

OTHER PUBLICATIONS

International Search Report; International Application No. PCT/IB2012/053819; Date of Actual Completion of International Search: Nov. 29, 2012; Date of Mailing of International Search Report: Jun. 12, 2012.

*Primary Examiner* — Kevin C Sirmons
*Assistant Examiner* — Amber Stiles
(74) *Attorney, Agent, or Firm* — Pearne & Gordon LLP

(57) ABSTRACT

The invention relates a safety IV catheter assembly comprising a catheter tube having a distal end and a proximal end; a catheter hub having a distal end and a proximal end; a needle extending through the catheter hub and the catheter tube having opposite proximal and distal ends defining an axial direction A, wherein the proximal end is joined to the needle hub and the distal end forms a needle tip and a change in profile is provided between the proximal and distal ends of the needle; and a tip protector assembly being arranged movably on the needle in-between the catheter hub and needle hub outside the catheter hub in an arrangement engaging with one or more second locking means provided on the catheter hub in its ready position, wherein the first arm is deflected radially outwards by the needle against a restoring force, wherein the tip protector assembly is configured to entrap the needle tip upon withdrawal of the needle from the catheter hub.

24 Claims, 12 Drawing Sheets

(56) References Cited

U.S. PATENT DOCUMENTS

| | | | |
|---|---|---|---|
| 6,749,588 B1* | 6/2004 | Howell et al. | 604/164.08 |
| 2005/0277879 A1* | 12/2005 | Daga | 604/110 |
| 2006/0270980 A1* | 11/2006 | Menzi | A61M 25/0637 604/110 |
| 2009/0281499 A1 | 11/2009 | Harding et al. | |
| 2010/0222749 A1* | 9/2010 | Baid | 604/263 |

* cited by examiner

NEEDLE TIP PROTECTOR ASSEMBLY FOR SAFETY IV CATHETER ASSEMBLY

CROSS-REFERENCES TO RELATED APPLICATIONS

This application is the national phase of International Application No. PCT/IB2012/053819 filed on Jul. 26, 2012, which claims the benefit of priority to Indian Patent Application No. 2108/DEL/2011 filed on Jul. 26, 2011. The entire disclosures thereof are incorporated herein by reference.

FIELD OF THE INVENTION

The present invention relates to a medical device such as, for example a safety in-travenous (IV) catheter assembly. In particular, the invention relates to a needle tip protector assembly for safety IV catheter assembly. More particularly the present invention relates to an IV catheter assembly with improved means and mechanism for withdrawing and securing the needle tip safely inside a tip protector assembly automatically after use providing protection from accidental needle pricks.

BACKGROUND OF THE INVENTION

Medical devices such as safety IV catheter assembly are used in healthcare facilities and hospitals. The IV catheter assembly of this kind is generally known and, for example, used to administer fluid and/or medicine to a patient or to take blood from a patient. Once a needle has been used, it becomes contaminated with the patient's blood and becomes a potential threat, especially for the health care workers, in the spread of infectious diseases. During surgery, handling of these sharp instruments can lead to accidental sticks or puncture wounds exposing the healthcare worker to the infections such as AIDS and hepatitis. The chances of needle stick are increased during an emergency with several aspects require to be handled. Likewise, during disposal, an exposed needle point may be and usually is a threat to the medical waste handler.

Various safety IV catheter assemblies have been developed to automatically cover and shield the needle tip after its withdrawal from the patient. These assemblies have taken a number of embodiments and have various degrees of elaboration. However, the safety mechanisms implemented in these assemblies increase costs of manufacture substantially and may malfunction, especially in a fluid-filled environment where it may stick or slip. Some of the known needle protecting systems requires multiple parts, which drives up the manufacturing cost for a disposable unit. The cost-benefit requirements of the medical industry call for an inexpensive needle protecting system which is disposable along with the needle.

Moreover, some IV catheter assemblies with the needle guard that have been developed sometimes fail to prevent occurrence of unintended needle stick injuries. Generally, in such assemblies a needle safety device or needle guard is arranged completely in a chamber defined by the catheter hub. In order to ensure correct protective function of the needle guard, it is necessary that the needle guard is secured steadily in its ready position while being secured inside in the catheter hub. However, such assemblies suffers from the problem of premature release of the needle guard from the catheter hubunder retracting forces applied on the needle while disengaging the needle hub from the catheter hub. In such a situation, the risk of accidental needle stick injury is a real threat to the users/practitioners. Moreover, such premature release and un-steadiness of the needle guard in the catheter hub affects its correct and effective function protecting the tip of the needle.

Hence, there is a constant need to address the aforementioned problems and to provide a medical device in particular an IV catheter assembly which provides reliable protection against accidental pricking from the sharp tip of the needle and which is easy and inexpensive to manufacture.

OBJECTS OF THE INVENTION

Therefore, the primary object of the present invention is to provide a protective system which is simple and dependable in its deployment, inexpensive to manufacture, expedient in its operation and effective in protecting a needle tip, and which ensures correct functioning even after longer shelf life.

It is another object of the present invention to provide an IV catheter assembly with improved means and mechanism for protection against accidental needle sticks and pricks.

It is another object of the present invention to provide an IV catheter assembly including a catheter hub without defining a chamber;

It is another object of the present invention to provide a tip protector assembly which can be fitted outside the catheter hub being lockingly secured therewith when the needle hub is in the retracted position.

It is another object of the present invention to provide an IV catheter assembly having a locking mechanism to secure the tip protector assembly together with the catheter hub when the needle hub is in the retracted position.

It is another object of the present invention to provide an IV catheter assembly having locking means to secure the tip protector assembly together with the catheter hub when the needle hub is in the retracted position.

It is another object of the present invention is to provide an IV catheter assembly with improved means and mechanism for withdrawing and automatically securing the needle tip safely inside a tip protector assembly after use.

It is another object of the present invention is to provide an IV catheter assembly with improved means and mechanism, which means and mechanism is irreversible once the tip protector assembly encloses the needle tip.

It is another object of the present invention is to provide an IV catheter assembly comprising a tip protector assembly that cannot be easily pulled off the needle tip once the needle tip is covered by the said tip protector assembly by application of even excessive external force.

Yet another object of the present invention is to provide an IV catheter assembly comprising needle safety means and mechanism that is simple in construction and cheap to manufacture.

Still another object of the present invention is to provide an IV catheter assembly which remains compact after the needle tip has been withdrawn from the medical device assembly and secured inside a tip protector assembly.

SUMMARY OF THE INVENTION

The present invention relates to a safety IV catheter assembly including a needle tip protector assembly with improved safety means and mechanism that automatically covers the sharp tip of the needle after withdrawal of the needle from the catheter tube and catheter hub preventing accidental needle sticks and pricks of a healthcare worker by the needle tip. The invention also relates to a tip protector assembly being arranged outside the catheter hub when the needle hub is in the retracted position.

According to one embodiment, a safety IV catheter assembly is provided comprising:

a catheter tube having a distal end and a proximal end; a catheter hub having a distal end and a proximal end; a needle extending through the catheter hub and the catheter tube having opposite proximal and distal ends defining an axial direction, wherein the proximal end is joined to the needle hub and the distal end forms a sharp tip and a change in profile is provided between the proximal and distal ends of the needle; a tip protector assembly being arranged movably on the needle in-between the catheter hub and needle hub including: a base portion having a needle passage extending in the axial direction from the proximal end of the base portion to a distal side of the base portion; a hollow enclosure formed by the extension of the base portion in a direction generally parallel to the axial direction; wherein the distal end of the hollow enclosure has a substantially circular opening allowing the needle to pass there-through; first and second arms made integrally within the said hollow enclosure and extending from the distal side of the base portion in an axial direction, wherein the region between the first and second arms and the hollow enclosure defines open space; at least one tension creating element surrounding partially and/or completely the said first and second arms in a region proximal to the distal ends thereof; at least one stopper element arranged in the base portion having an axial bore with a dimension adapted to the principal outer profile of the said needle; and one or more first locking means to lockingly engage the tip protector assembly outside the catheter hub in an arrangement engaging with one or more second locking means provided on the catheter hub in its ready position, wherein the first arm is deflected radially outwards by the needle against a restoring force.

Preferably, the outer profile of the tip protector assembly in particular the hollow enclosure has a substantially cylindrical shape or a tube like shape. It is to be noted however, that the outer profile of the tip protector assembly need not necessarily be cylindrical in shape or tube like shape and can have any other shape such as a rectangular, square or any other suitable shape.

According to an embodiment, the hollow enclosure may be defined as a circular wall surrounding the first and second arms of the tip protector assembly. The distal end of the hollow enclosure has a peripheral surface which acts as a locking surface to engage with one or more second locking means provided on the catheter hub when the tip protector assembly is in its ready position.

According to an embodiment, the first locking means provided on the tip protector assembly include one or more locking protrusions, for example disc-like locking protrusion or at least part annular disc like locking protrusion or combination thereof provided in a distal region on the inner surface of the hollow enclosure of the tip protector assembly. According to a preferred embodiment, the protrusion is of partcircular, in particular semi-circular shape. The locking protrusions are adapted to engage with second locking means provided on the outer wall of the catheter hub. The second locking means include one or more locking depressions for example, a locking recess/groove or at least part annular locking recess/groove or combination thereof.

According to an embodiment, the first locking means include one or more locking depressions and second locking means include one or more locking protrusions.

According to an embodiment, the first and second locking means include a combination of one or more locking protrusions and one or more locking depressions.

According to an embodiment, the first and second locking means include one or more locking lugs.

According to an embodiment, the first and second locking means include one or more locking threads.

According to an embodiment, the first and second locking means include a combination of one or more locking lugs and one or more locking threads.

According to an embodiment, the first and second locking means are adapted to engage rotatably in at least first direction in a locking arrangement securing the tip protector with the catheter hubbeing secured outside the body of the said catheter hub when the needle is in its ready position. In order to disengage the tip protector assembly in its tip protecting position from the catheter hub, the first and second locking means are disengaged by rotating in at least second direction opposing the first direction.

According to an embodiment, the first arm includes a first free end and the second arm includes a second free end extending generally axially in a distal direction from the base portion. The first free end extends beyond the second free end and overlaps the second free end by an angled end section including a length and width configured to retain the tip of the needle within a tip holding space so that in protected position the angled end section abuts the needle, in particular the tip of the needle. The length and width of the angled end section are larger than the maximum outer profile of the needle and/or its diameter and adapted to confine the needle tip within a tip holding space.

As a preferred alternative, angled end section of the first arm may have an undercut for catching the needle tip. Further, the portion forming the angled end section may be made of a second material different from the first material forming, for example the first and second arms of the tip protector assembly such that harder plastic material or portion reinforced with metal material or the like so that the needle abutting the angled end section cannot pierce through it and be retained firmly in the needle tip holding space even under application of excessive force.

According to an embodiment, each of the at least one side of the inner walls of the first and second arms of the tip protector assembly has internal recess close to the base portion thereof forming a cavity or cut out. The extension of the region above the said internal recess towards the distal end in the axial direction forms protective side-flaps in at least one side thereof providing an enclosure for the needle passing therethrough. The protective side-flaps provided on the first and second arms surround the needle shaft when passing through the first and second arms. The distal end of each of the internal recess in the first and second arms defines a shoulder. The side-flaps help prevent the needle tip from protruding sideways out of the tip protector assembly, thereby further increasing the protective function thereof. Moreover, the internal recesses provided in the arms facilitate deflectability and also improves restoration capabilities thereof. In particular, the internal recess provided in the first arm helps in improving deflectability as well as the restoration properties of first arm when the distal angled end thereof is no longer supported on the needle shaft. Thus, the internal recess increases the deflectability of the arms in the regions it is provided and thereby reduces the restoring force acting thereon, in particular on the angled end section of the first arm while it is being supported by the needle shaft. This allows the needle to be moved more easily relative to the first and second arms and in particular relative to the angled end section, as the frictional force acting on the needle is reduced. In the embodiment, where a floating stopper element e.g. a floating disk or washer is provided as a stopper element the shoulder formed by distal end of the said internal recess in the first and second arms act as movement limiting means.

According to an embodiment, a tension creating element surrounds the first and second arms of the tip protector assembly, for example an elastic band in between the proximal and distal region of the first and second arms, in particular in a region proximal to the distal end of the first and second arms. The tension creating element exerts a restoring force on the first and second arms when tip protector assembly is in its ready position i.e. when the first and second arms are spread apart by the needle extending all the way through the tip protector assembly. Once the needle shaft no longer supports the angled end section of the first arm i.e. when the tip protector assembly is in its tip protecting position, the tension creating element aids the repositioning of the first arm back into axial alignment with the axial direction. This repositioning is necessary so that the angled end section can block the needle tip from axially sliding out of the tip protector assembly. In addition, the tension creating element defines a tip holding enclosure between the first and second arms and thus helps to prevent the needle shaft and the needle tip from protruding sideways out of the tip protector assembly. Thus, the tension creating element adds to the protective effect of the tip protector assembly.

In a preferred alternative, the tension creating element partly surrounds the first and second arms of the tip protector assembly i.e. instead of surrounding the two arms the tension creating elements biases the two arms by a linear biasing action.

In another preferred alternative, the tension creating element have the structure forming a link connecting the said first and second arms and which may be positioned and/or arranged in at least one of the either sides of first and second arms of the tip protector assembly.

In yet another preferred alternative, the tension creating element may have the structure forming a link connecting the said first and second arms and which may be positioned and/or arranged in both sides of first and second arms of the tip protector assembly.

In one embodiment, the tension creating element includes the structure in the form of a ring.

In one embodiment, the tension creating element may not be a separate component of the tip protector assembly and can be integrally made therein. It may be made from an elastic material and/or materials having elastic properties, for example, silicone, rubber or the like.

In one embodiment, the tension creating element may be arranged or positioned in any of the region in between the proximal and distal regions of the first and second arms of the tip protector assembly.

The change in profile may be defined as a needle section having a different dimension than the nominal diameter and may be created using various means. The change in profile may be for example, an enlargement and it may be made by crimping a portion of the needle either only on one side or point on the circumference of the needle or alternatively along both sides or symmetrically along the circumference of the needle.

In a preferred alternative, the change in profile may be formed in the form of a shoulder, bulge formed as an annular widening and by adding material onto the outer surface of the needle or by adding a sleeve to the needle for example, by welding, gluing or soldering etc. The added material may include a metal material, a plastic material, adhesive, resin or the like. In the case of the added material being metal material, the change in profile may, for example, be formed by build-up welding or by soldering of the additional material onto the needle. Alternatively, the additional material could be glued to the needle. The change in profile in the form of an enlargement may be referred to as a crimp, a sleeve, annular sleeve, part annular sleeve, a bulge, a section of the needle with added material or combinations thereof. Further, the inner profile of the needle can either be reduced in the region of the change in profile, for example, if the change in profile is formed by crimping, or it can be substantially constant throughout the length of the needle, for example, if the change in profile is formed by applying additional material to the needle shaft.

In one embodiment, the needle shaft may also be formed with a slit forming an opening arranged distally or proximally from the change in profile therein. The opening may be formed by a small slit which is cut into the needle shaft and which extends in axial direction for a small distance, for example 0.3 to 1 mm. The opening is just large enough in order to provide an early blood flashback function close to the needle tip within the catheter tube such that the medical practitioner can recognize that needle has been placed correctly within the patient's vein. In case of correct, positioning of the needle, blood pours out of the opening within the needle shaft into the space between the needle shaft and the inner wall of the transparent catheter tube and visible to the medical practitioner.

In one embodiment, a groove may be provided either in the inner wall of one of the first and second arms extending substantially in the axial direction from the base portion. The groove acts as a guide groove for the needle shaft and aids the axial movement of the needle shaft relative to the tip protector assembly. Moreover, the needle shaft is prevented from sliding sideways, in particular off the angled end section of the first arm. Such a sideways movement would significantly increase the force required to move the needle shaft relative to the tip protector assembly, which would prevent a correct functioning of the tip protector assembly. Alternatively, the guide groove can be provided in both the first and second arms.

In one embodiment, the tip protector assembly is made from a unitary plastic material or, or an elastomer or thermoplastic or any combination thereof such as thermoplastic elastomer. In other embodiments, the tip protector assembly is made from multi-pieces and includes materials such as metal and/or plastic or any combination thereof. For example, either of the first and second arms or both may be made of a resilient material or plastic material or metal material or combination thereof.

In one embodiment, the stopper element is arranged within the base portion and can be integrally formed within the base portion of the tip protector assembly. The stopper element is made of a second material different from a first material of the base portion and has a through-bore with a profile which is adapted to the principal outer profile of the needle shaft. Preferably, the stopper element defines an axial bore having a cross-section adapted to the principal profile of the needle but being smaller than the radial dimension of the change in profile in the form of an enlargement forming the engagement means configured on the needle shaft. The stopper element is preferably arranged such that its axial-bore is in general alignment with the needle passage of the tip protector assembly.

According to an embodiment, the stopper element surrounds the needle. The length of the stopper element, i.e. its dimension seen in the axial direction, may vary. As such, the stopper element can, for example, be disk or a ring or a washer or a tube. However, it is to be understood that the outer profile of the stopper element does not have to have a circular outer profile. It is also possible that the outer profile of the stopper element is of non-circular form, for example, of oval or polygonal shape or other suitable geometric shape.

According to an alternative, it is also possible that the stopper element only partly surrounds the needle. In this case, the stopper element could have the shape of a slotted disk, ring or tube.

As yet another preferred alternative, the stopper element may also be arranged loosely on the needle between the two arms of the tip protector assembly and floating on the needle shaft and can be held in the area defined by the internal recess of the first and second arms. As such the stopper element may be formed by a tube-like element. It can be held by holding means, like one or more locking protrusions or locking depressions in a predetermined section of the tip protector assembly, for example in a region proximal to the base portion of the tip protector assembly. Alternatively, the stopper element can be arranged in floating condition in a pre-determined section in between the first and second arms of the tip protector assembly anywhere in between the proximal section and distal section thereof along the line of needle passage configured therein.

To define the reference to first material and second material as used herein, preferably, the second material is of greater hardness and/or stiffness than the first material. For example, the first material could be a plastic material and the second material could consist of a metal, a harder fiber material, a rubber material or a ceramic, or any other type of suitable material which is stiff and not as easily distortable as the first material.

Yet another embodiment of the present invention relates to methods of making/assembling and using an IV catheter assembly including the tip protector assembly when the tip protector assembly is in its ready position.

Further advantageous embodiments of the invention and preferred assemblies for carrying out the invention are disclosed in connection with the accompanying drawings.

BRIEF DESCRIPTION OF THE DRAWINGS

The present invention will now be explained in more detail in the following with reference to preferred embodiments and to the accompanying drawings in which are shown.

DETAILED DESCRIPTION OF THE INVENTION

As used herein, the term 'proximal' refers to a region of the assembly/device or a location on the assembly/device which is closest to, for example, a medical practitioner using the assembly/device. In contrast to this, the term 'distal' refers to a region of the assembly/device which is farthest from the medical practitioner, for example, the distal region of a needle will be the region of a needle containing the needle tip which is to be inserted e.g. into a patient's vein.

Further, as used herein the term first and second are merely identifiers and do not necessarily limit and/or restrict the features with such identifiers. For example, when viewed from another perspective, the first arm may be called the second arm and vice-versa.

The various embodiments of present invention are directed to an IV catheter assembly including a tip protector assembly.

Figure 1:
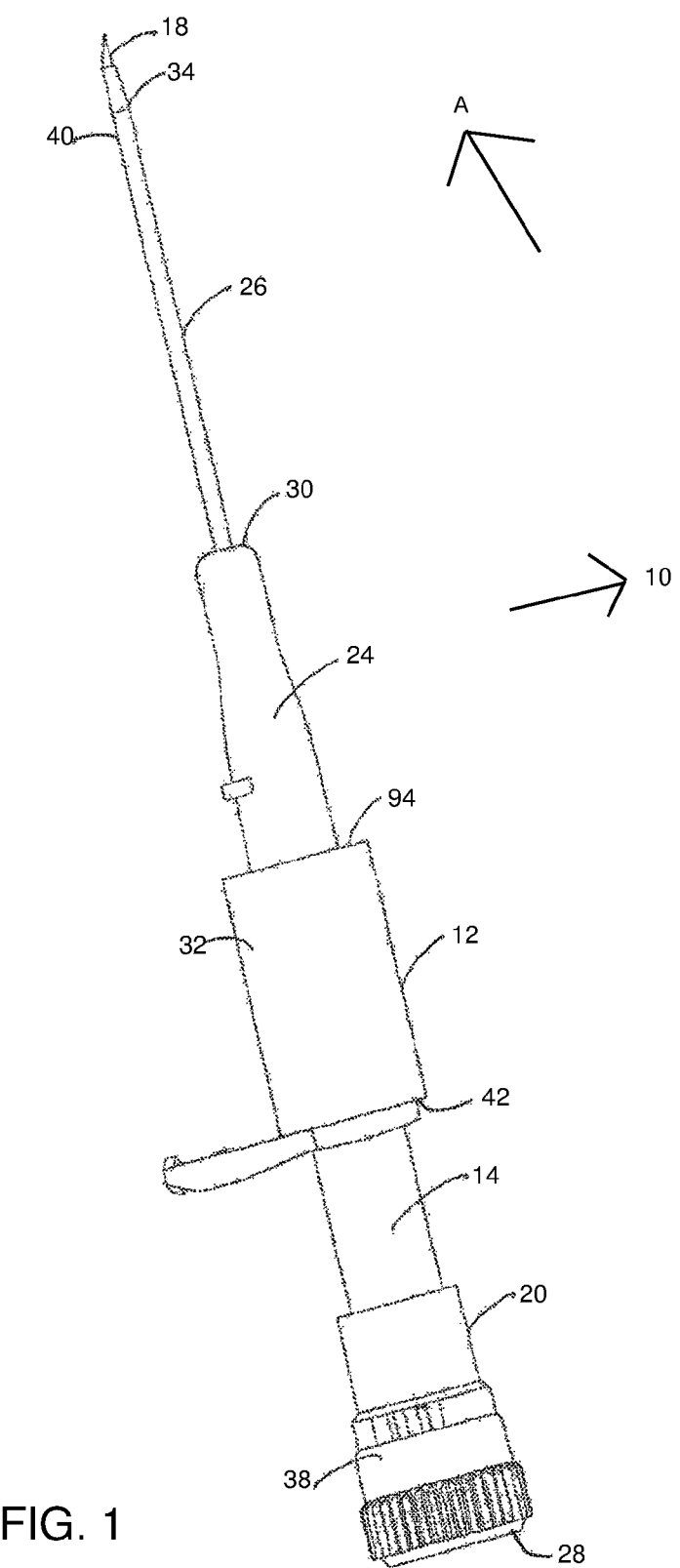
FIG. 1 illustrates an IV catheter assembly in accordance with the present invention illustrating the tip protector assembly in its ready position.

FIG. 1 shows an IV catheter assembly 10 in accordance with the invention prior to use illustrating the tip protector assembly 12 being in its ready position. The catheter assembly includes a catheter tube 26 having distal 30 and proximal 28 ends and a catheter hub 24 attached to the catheter tube 26 at the proximal end 28 of the catheter tube 26. The catheter assembly includes a needle 14 extending through the catheter hub 24 and catheter tube 26 defining an axial direction A. The needle 14 has distal 30 and proximal 28 ends, wherein a sharp needle tip 18 is formed at the distal end 30 of the needle. A needle hub 20 is attached to the proximal end 28 of the needle. The catheter assembly further includes a tip protector assembly 12 movably arranged on the needle 14 in between the needle hub 20 and catheter hub 24. As shown, the tip protector assembly 12 in a locking arrangement with the catheter hub 24 is, thus, secured outside the body of the said catheter hub 24 when the needle 14 is in its ready position. Prior to use of the catheter assembly the needle 14 extends all the way through the thorough bore 44 of the tip protector assembly 12 passing through the catheter hub 24 as well as catheter tube 26 and the needle tip 18 protrudes from a distal end 30 of the catheter tube 26. As mentioned above, this position of the needle 14 is referred to as the 'ready position' in this context.

The needle shaft 16 has a generally constant principal profile, except for a change in profile 34, for example in the form of an enlargement 36 of the radial dimension of the needle 14 in at least one direction as compared to the principal profile. Preferably, the change in profile 34 is provided in the region closer to the proximal end 28 of the needle. The change in profile 34 may be defined as a needle 14 section having a different dimension than the nominal diameter and may be created using various means and which forms an engagement means. The change in profile 34 can be made, for example, by crimping the needle shaft 16. The function of the engagement means will be discussed in more detail further below.

Figure 2A:
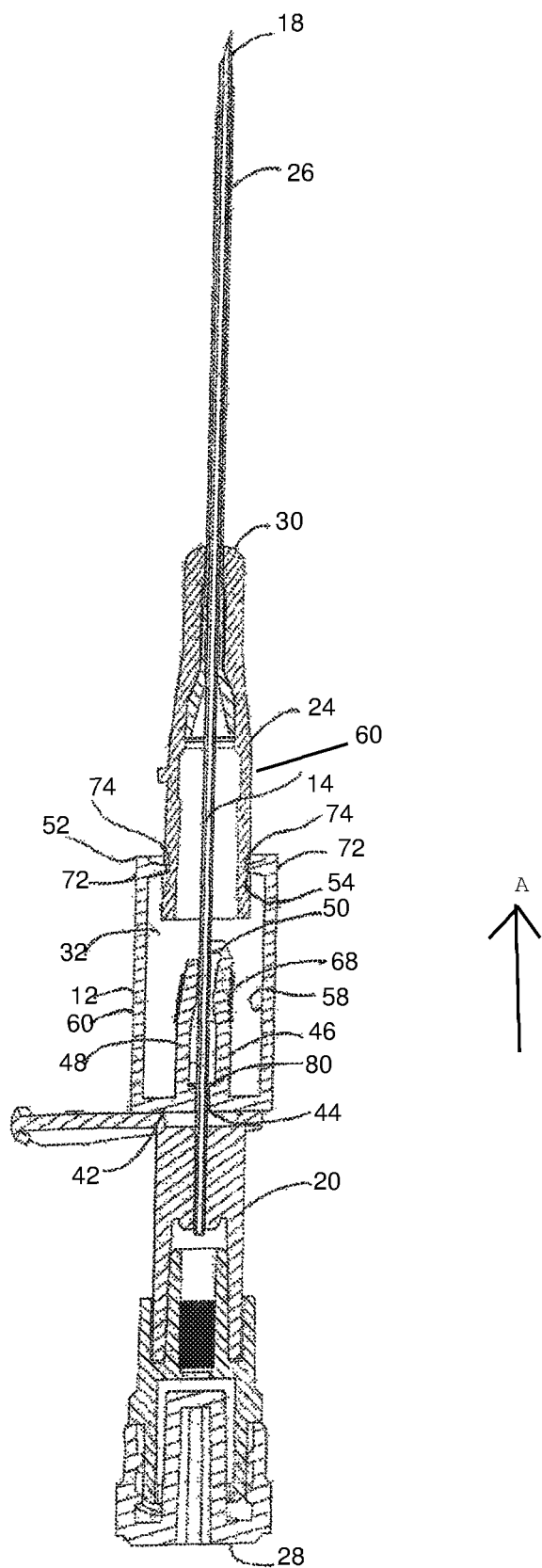
FIG. 2A is a sectional illustration of the side view of an IV catheter assembly in accordance with the present invention illustrating the tip protector assembly in its ready position.

FIG. 2A shows side view of an IV catheter assembly 10 illustrating the tip protector assembly 12 in its ready position according to one embodiment of the invention. As shown the tip protector assembly 12 is movably arranged on the needle shaft 16 outside the catheter hub 24 by first locking means 52 provided in the tip protector assembly 12 engaging with the second locking means 54 provided on the outer wall of the catheter hub 24. The first locking means 52 include one or more locking protrusions 72, for example at least a pair of part annular disc likes locking protrusions 72 or at least a pair of locking lugs 76 in a direction opposing each other. The first locking means 52 are provided in the inner wall 58 of the hollow enclosure 32 proximal to the distal end 30. The second locking means 54 include locking depressions 74 in the form of for example, at least a pair of locking recess or grooves 74 or a pair of part annular grooves 74 in a direction opposing each other receiving the first locking means 52 in the ready position of the tip protector assembly 12. The second locking means 54 are configured on the outer wall of the catheter hub 24 in a region close to the proximal end 28. It is to be noted that instead of the locking depressions 74 provided on the outer wall of the catheter hub 24 it is also possible to provide one or more locking protrusions 72 or combination of either a locking protrusion 72 or a locking depression 74 in the outer wall of the catheter hub 24.

As can be seen, the region between the first 46 and second 48 arms and the hollow enclosure 32 defines open space 56. The tip protector assembly 12 includes an outer wall 60, a base portion 42 at a proximal end of said tip protector assembly 12 having a through bore 44 for receiving the needle 14 extending towards distal end in an axial direction A. The first 46 and second 48 arms extend from a distal side/end of the base portion 42 generally in the axial direction A. The profile of the through bore 44 is adapted to the principle outer profile of the needle. The first arm 46 is longer than the second arm 48 and has a distal section which is angled towards the second arm 48 and substantially overlaps with the second arm 48, forming the angled end section 50. The angled end section 50 preferably has an undercut for catching the needle tip 18. In its ready position, the angled end section 50 of the first arm 46 is supported on the needle shaft 16 against a restoring force exerted by for example, a tension creating element 68. Since in a preferred embodiment, the first 46 and second 48 arm is made of resilient material, such as plastic material having elastic properties, it is to be understood that the restoring force can also be exerted by the first 46 and second 48 arm.

In contrast to the first arm 46 and because of lack of distal angled end section 50, the second aim 48 has less deflectability than the first arm 46 when the needle 14 extends through the tip protector assembly 12. Nevertheless, in order to facilitate delectability of both the first 46 and second 48 arms, each of the at least one side of the inner walls of the first 46 and second 48 arms of the tip protector assembly 12 has an internal recess 62 close to the base portion 42 thereof forming a cavity or cut out 64 (not shown). The extension of the region above the said internal recess 62 towards the distal end 30 in the axial direction A forms protective side-flap 66 (FIGS. 2A to 3B) in at least one side thereof providing an enclosure for the needle 14 passing therethrough in both the first 46 and second 48 arms. The protective side-flaps 66 provided in at least one side of the first 46 and second 48 arms surround the needle shaft 16 when passing through the first 46 and second 48 arms. Moreover, the protective side-flaps 66 help prevent the needle tip 18 from protruding sideways out of the tip protector assembly 12, thereby further increasing the protective function thereof It is to be understood that the protective side-flap 66 can be provided on the either sides of the first 46 and second 48 arms in a similar manner. Further, such recess 74 can be formed both on the inner and outer walls of the first 46 and second 48 arms or in a combination of the inner and outer walls of the first 46 and second 48 arms.

Figure 2B:
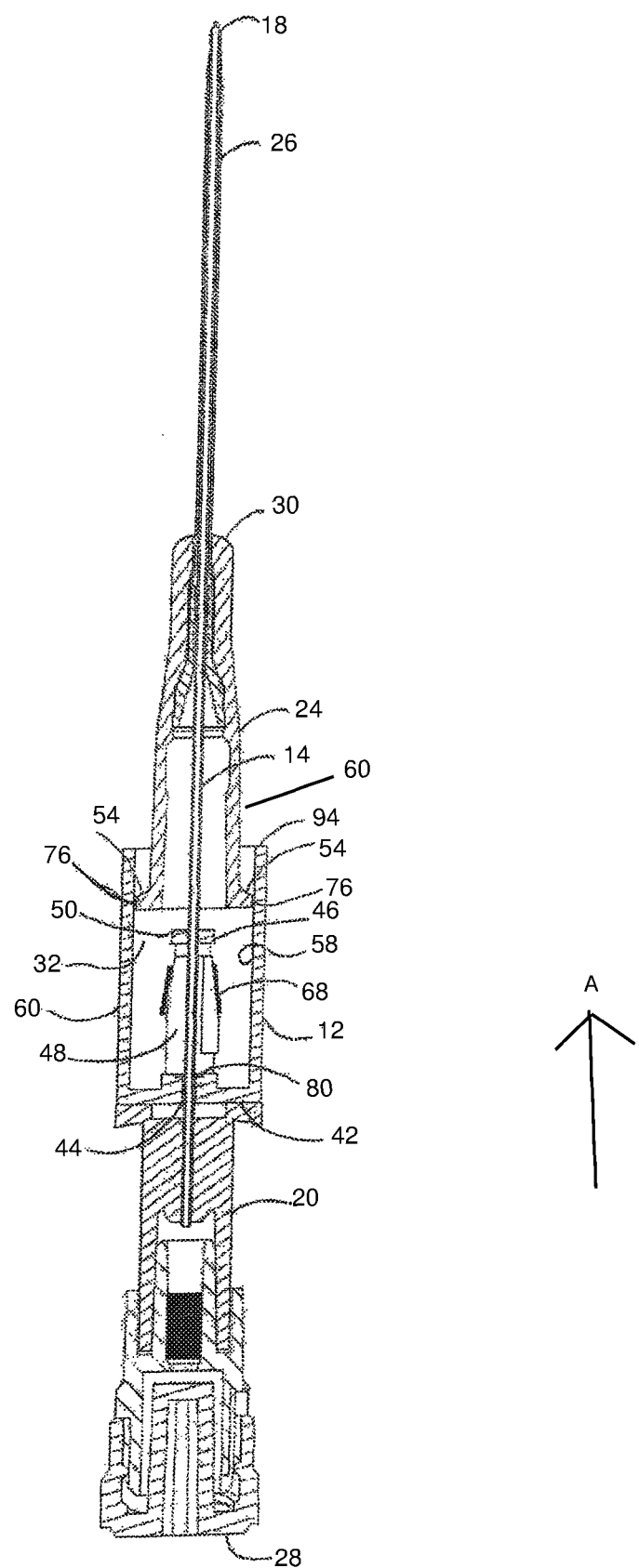
FIG. 2B is a sectional illustration of the front view of an IV catheter assembly in accordance with the present invention illustrating the tip protector assembly of FIG. 2A in its ready position.

As shown in FIG. 2B, in addition to at least a pair of grooves or recess 74 the second locking means 54 include at least a pair of locking lugs 76 which are adapted to engage with the peripheral surface 94 forming a locking surface provided on the distal end 30 of the hollow enclosure 32 when the tip protector assembly 12 is in its ready position. As shown, the pair of locking lugs 76 is configured on outer wall of the catheter hub 24 at the proximal end 28 in a direction opposing each other. The engagement of the first 52 and second 54 locking means help the tip protector assembly 12 to lockingly engage with the catheter hub 24 being secured outside the body of the said catheter hub 24 in its ready position prior to use preventing movement of the tip protector assembly 12 before the needle tip 18 is safely received inside the first 46 and second 48 arms of the tip protector assembly 12. It is to be noted that instead of the locking lugs 76 provided on the catheter hub 24 it is also possible to provide one or more locking depressions 74 or combination of either a locking lug 76 or a locking depression 74. Further as shown, it is to be understood that the tip protector assembly 12 including first 46 and second 48 arms may be made of a transparent plastic material or transparent elastomer material or the like. For ease in understating the needle 14 has been shown passing through the through bore 44 of the base portion 42 extending in axial direction A.

Figure 3A:
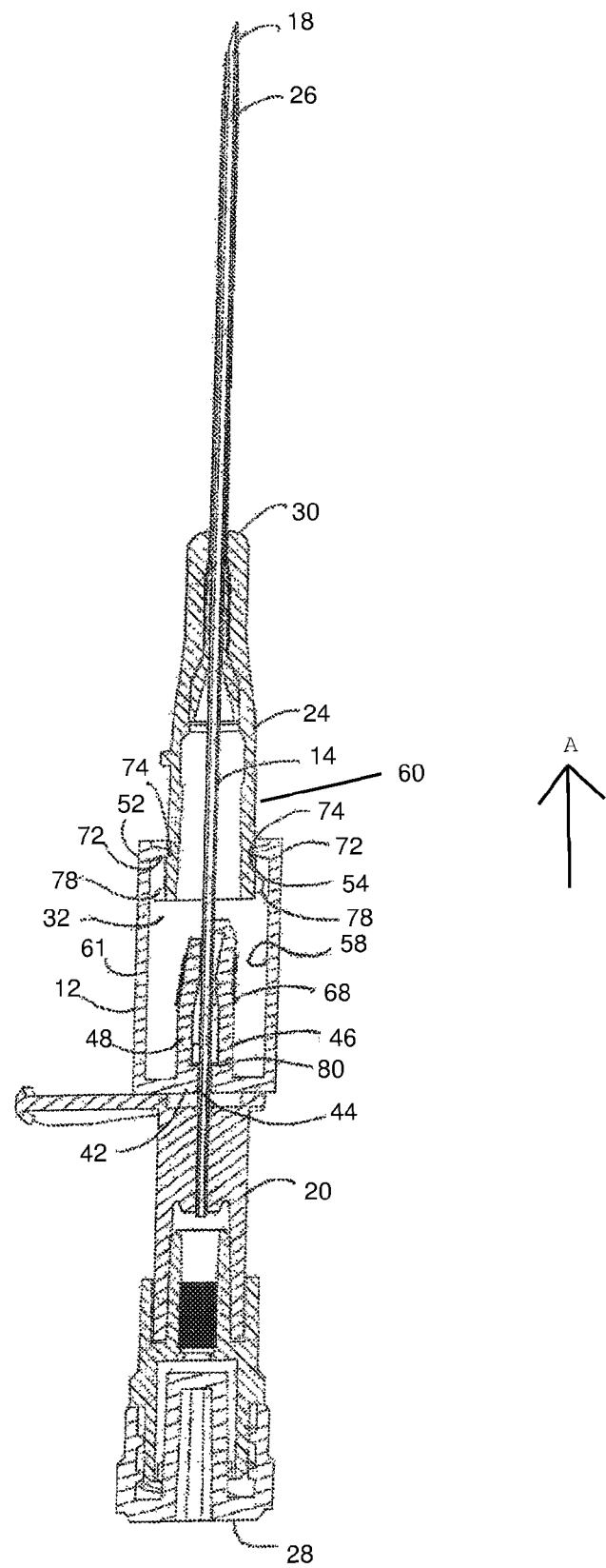
FIG. 3A is a sectional illustration of the front view of an IV catheter assembly in accordance with the present invention illustrating the tip protector assembly in its ready position in an another embodiment.

FIG. 3A shows front view of an IV catheter assembly 10 illustrating the tip protector assembly 12 in its ready position according to another embodiment of the invention. As shown the tip protector assembly 12 is movably arranged on the needle shaft 16 outside the catheter hub 24 by first locking means 52 provided in the tip protector assembly 12 engaging with the second locking means 54 provided on the outer wall of the catheter hub 24. The first locking means 52 include one or more locking protrusions 72 in the similar manner as explained in FIG. 2A and received in the second locking means 54 provided on the outer wall of the catheter hub 24.

Figure 3B:
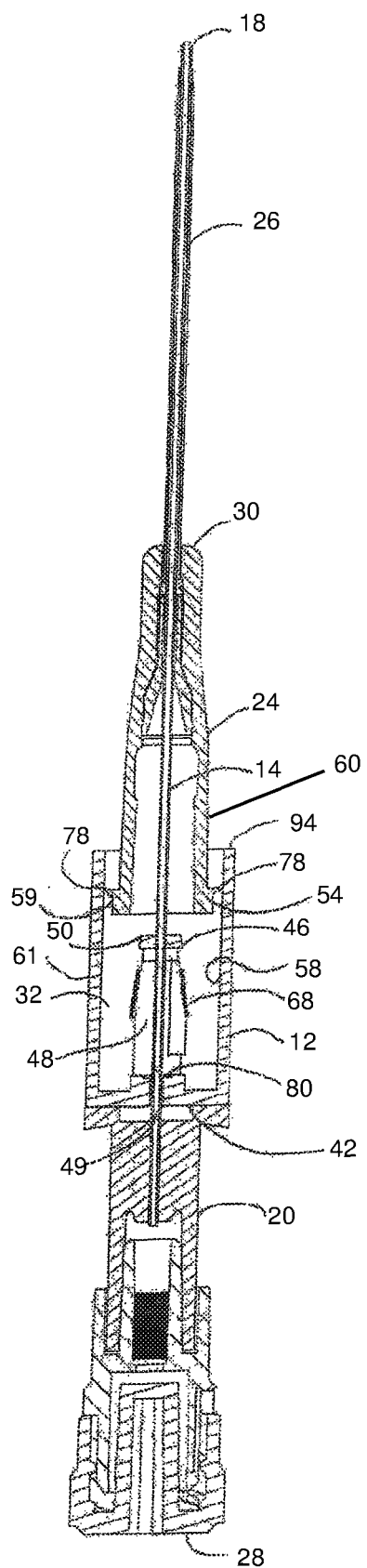
FIG. 3B is a sectional illustration of the side view of an IV catheter assembly in accordance with the present invention illustrating the tip protector assembly of FIG. 3A in its ready position.

As shown in FIG. 3B, in addition to at least a pair of grooves 74 the second locking means 54 includes locking threads 78 on the outer wall of the catheter hub 24 in the region of proximal section 38. The locking threads 78 are configured as annular locking thread 78 or at least part annular locking thread 78 on the outer circumferential wall of the catheter hub 24. The locking thread 78 is adapted to engage with peripheral surface 94 of the hollow enclosure 32 provided on the distal end 30 of the hollow enclosure 32 which forms a locking surface when the tip protector assembly 12 is in its ready position. As such, the first 52 and second 54 locking means are adapted to engage rotatably in at least first direction in a locking arrangement securing the tip protector assembly 12 with the catheter hub 24 being secured outside the body of the said catheter hub 24 in its ready position. In order to disengage the tip protector assembly 12 from the catheter hub 24 when the tip protector assembly 12 is in its tip protecting position, the first 52 and second 54 locking means are disengaged by rotating in at least second direction opposing the first direction. For ease in understating the needle 14 has been shown passing through the through bore 44 of the base portion 42 extending in axial direction A.

It is to be noted that the first locking means 52 may include one or more locking depressions 74 and second locking means 54 include one or more locking protrusions 72. As another alternative, the first 52 and second 54 locking means include a combination of one or more locking protrusions 72 and one or more locking depressions 74. As another alternative, the first 52 and second 54 locking means include one or more locking lugs 76. As another alternative, the first 52 and second 54 locking means include one or more locking threads 78. As yet another alternative, the first 52 and second 54 locking means include a combination of one or more locking lugs 76 and one or more locking threads 78.

Even though the first 46 and second 48 arms have certain elastic properties, a tension creating element 68, for example a rubber band, may surround preferably a distal section of the first 46 and second 48 arms such that deflection of at least the first arm 46 occurs mainly against a restoring force of the tension creating element 68. One or more locking protrusions 72 forming tapered outer surfaces 70 extending along the outer periphery of the first 46 and second 48 arms are provided in order to position the tension creating element 68 on the first 46 and second 48 arms (FIGS. 2A to 3B and 4B). Because of the tapered outer surfaces 70 the tension creating element 68 is prevented from sliding off the distal sections of the first 46 and second 48 arms, when the first 46 and second 48 arms are spread apart against a restoring force of the tension creating element 68. In a preferred alternative, the tension creating element 68 may not be a separate component of the tip protector assembly 12 and can be integrally made therein.

In another preferred alternative, the tension creating element 68 partly surrounds the first 46 and second 48 arms are (not shown) of the tip protector assembly 12 i.e. instead of surrounding the two arms the tension creating elements 68 biases the two arms by a linear biasing action. In another preferred alternative, the tension creating element 68 have the structure forming a link connecting the said first 46 and second 48 arms (not shown) and which may be positioned and/or arranged in at least one of the either sides of first 46 and second 48 arms of the tip protector assembly 12. In yet another preferred alternative, the tension creating element 68 may have the structure forming a link connecting the said first 46 and second 48 arms (not shown) and which may be positioned and/or arranged in both sides of first 46 and second 48 arms of the tip protector assembly 12.

As is best seen in FIGS. 2A to 3B, 4B and 5, a stopper element 80 is provided in the base portion 42 or on the distal side/end 30 of the base portion 42, for example by insert molding. The stopper element 80 has an axial bore 82 which is aligned with the thorough-bore 44 of the base portion 42. The axial bore 82 has a circular cross-section with its diameter being slightly larger than the principle diameter of the proximal section 38 of the needle shaft 16 relative to the stopper element 80. More specifically, the cross-section of the axial bore 82 of the stopper element 80 is adapted to the principal profile of the needle shaft 16 such that the stopper element 80 can slide along the needle shaft 16 with minimum friction. At the same time the diameter of the axial bore 82 is not only smaller than that of the needle passage 22 but also smaller than the maximum dimension of the change in profile 34 of the needle shaft 16, e.g. in the form of enlargement 36, in order to prevent the enlargement 36 from passing through the axial bore 82 and, thus, to prevent the tip protector assembly 12 from sliding off the needle.

Preferably, such a stopper element 80 would be made of a second material of a greater hardness and/or stiffness different from the first material of the base portion 42, such that the stopper element 80 withstands greater force exerted by the change in profile 34 of the needle 14 upon withdrawal of the needle 14 from the catheter, thereby more effectively preventing the change in profile 34 of the needle 14 from passing through the base portion 42 and thus more effectively preventing the tip protector assembly 12 from sliding off the needle. Preferably, the stopper element 80 has a disk-like shape, similar to a washer or ring and is made of hard plastic, metal or ceramic and it can also be made out of any other material which is stiff and which cannot easily be distorted.

The fact that the stopper element 80 is made from a second material which is harder and less easily distortable than the first material of the base portion 42, has the effect that the tip protector assembly 12 is secured more effectively on the needle shaft 16 and can be retained even if excessive external force is applied when pulling on the needle, as the change in profile 34 in the form of, for example an enlargement 36 acting as engagement means is prevented from being pulled through the base portion 42 of the tip protector assembly 12. Hence, it is less likely that the tip protector assembly 12 is removed from the needle tip 18 accidentally and, as a result, the tip protector assembly 12 provides a better protection against accidental pricking and thus increased safety for the person handling the catheter assembly.

Further, it is to be understood, that the stopper element 80 need not be arranged in the base portion 42 itself, but can also be arranged at the distal side/section thereof between the first 46 and second 48 arms are of the tip protector assembly 12. Thus, the position of the stopper element 80 in between the first 46 and second 48 arms can be selected freely.

As a preferred alternative, the stopper element 80 may also be arranged loosely on the needle 14 between the two arms of the tip protector assembly 12 and floating on the needle shaft 16 and can be held in the area defined by the internal recess 62 of the first 46 and second 48 arms are (not shown). As such the stopper element 80 may be formed by a tube-like element. It can be held by holding means, like one or more locking protrusions or locking depressions in a predetermined section of the tip protector assembly 12, for example in a region proximal to the base portion 42 of the tip protector assembly 12. Alternatively, the stopper element 80 can be arranged in floating condition in a pre-determined section in between the first 46 and second 48 arms of the tip protector assembly 12 anywhere in between the proximal section 38 and distal section thereof along the line of needle passage 22 configured therein.

Figure 4A:
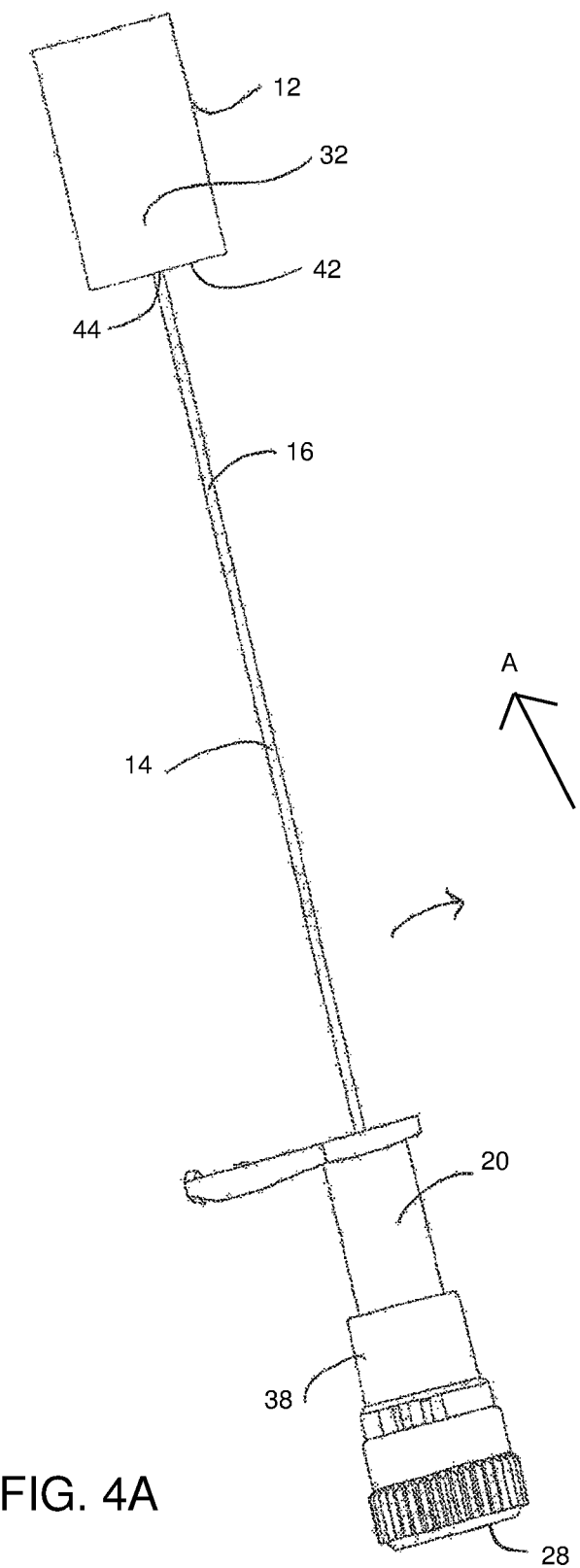
FIG. 4A illustrates a needle, needle hub and tip protector assembly in its protective position being removed from the IV catheter assembly of FIG. 1.
Figure 4B:
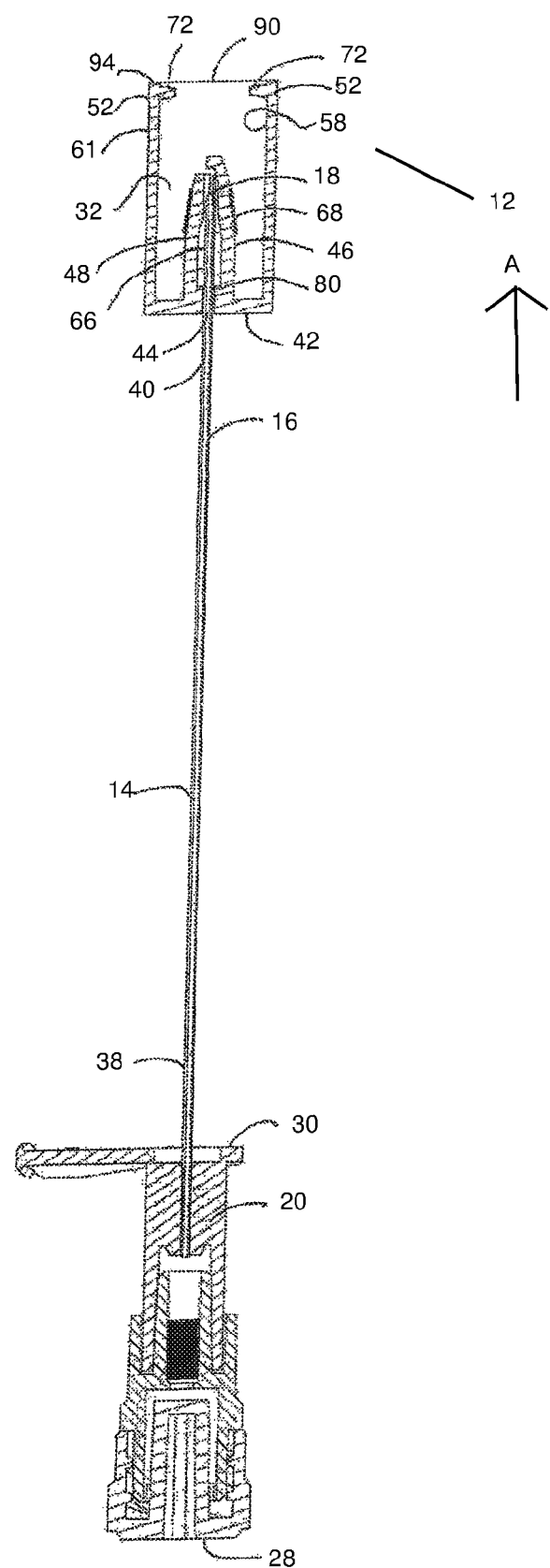
FIG. 4B is a sectional illustration of a needle, needle hub and tip protector assembly in its protective position being removed from the IV catheter assembly of FIG. 1.

As shown in FIGS. 4A and 4B, the purpose of the needle tip 18 protector assembly 12 is to cover the needle tip 18 after placement of the catheter tube 26 in and withdrawal of the needle 14 from the patient's vein. This position can be referred to as 'tip protecting position'. When the needle 14 is withdrawn from the catheter tube 26 and catheter hub 24 the needle shaft 16 moves relative to the tip protector assembly 12 being lockingly engaged with the catheter hub 24 by the first 52 and second 54 locking means being secured outside the body of the said catheter hub 24 in its ready position. Once the needle tip 18 is received in the tip protector assembly 12 and passes the angled end section 50 of the first arm 46, at this point the angled end section 50 is no longer supported on the needle shaft 16 and a restoring force ensures that the first arm 46 of the needle 14 is moved back into alignment with the axial direction A into its tip protecting position so that the needle tip 18 is blocked by the angled end section 50 of the tip protector assembly 12.

At the same time, it is to be understood that the change in profile 34 e.g. in the form of the enlargement 36 engages with the base portion 42 of the needle shaft 16 and in particular with the stopper element 80 therein such that the tip protector assembly 12 can be pulled out of the catheter hub 24 together with the needle. In such position, the first locking means 52 provided on the tip protector assembly 12 also disengage from the second locking means 54 provided outside the catheter hub 24, preferably by the pulling force acting on the tip protector assembly 12 via the needle 14 and the stopper element 80. An axial movement of the needle 14 relative to the tip protector assembly 12 is now limited, as the angled end section 50 blocks the needle tip 18 and the base portion 42 in particular the stopper element 80 therein prevents the needle tip 18 from being removed via the base portion 42 and thus the needle tip 18 is safely surrounded by the tip protector assembly 12, as is shown in FIGS. 4A and 4B.

It is to be understood that because of the engagement between the first locking means 52 and second locking means 54, the tip protector assembly 12 is prevented from axial movement relative to the catheter hub 24 and effectively engaged with the catheter hub 24 being secured outside the body of the said catheter hub 24 when the needle 14 is in its ready position until a pulling force exerted by the needle 14 on the base portion 42 of the tip protector assembly 12 via the change in profile 34 of the needle 14 upon withdrawal of the needle 14 from the catheter hub 24 becomes great enough to disengage the first locking means 52 from the second locking provided on the catheter hub 24.

Figure 5:
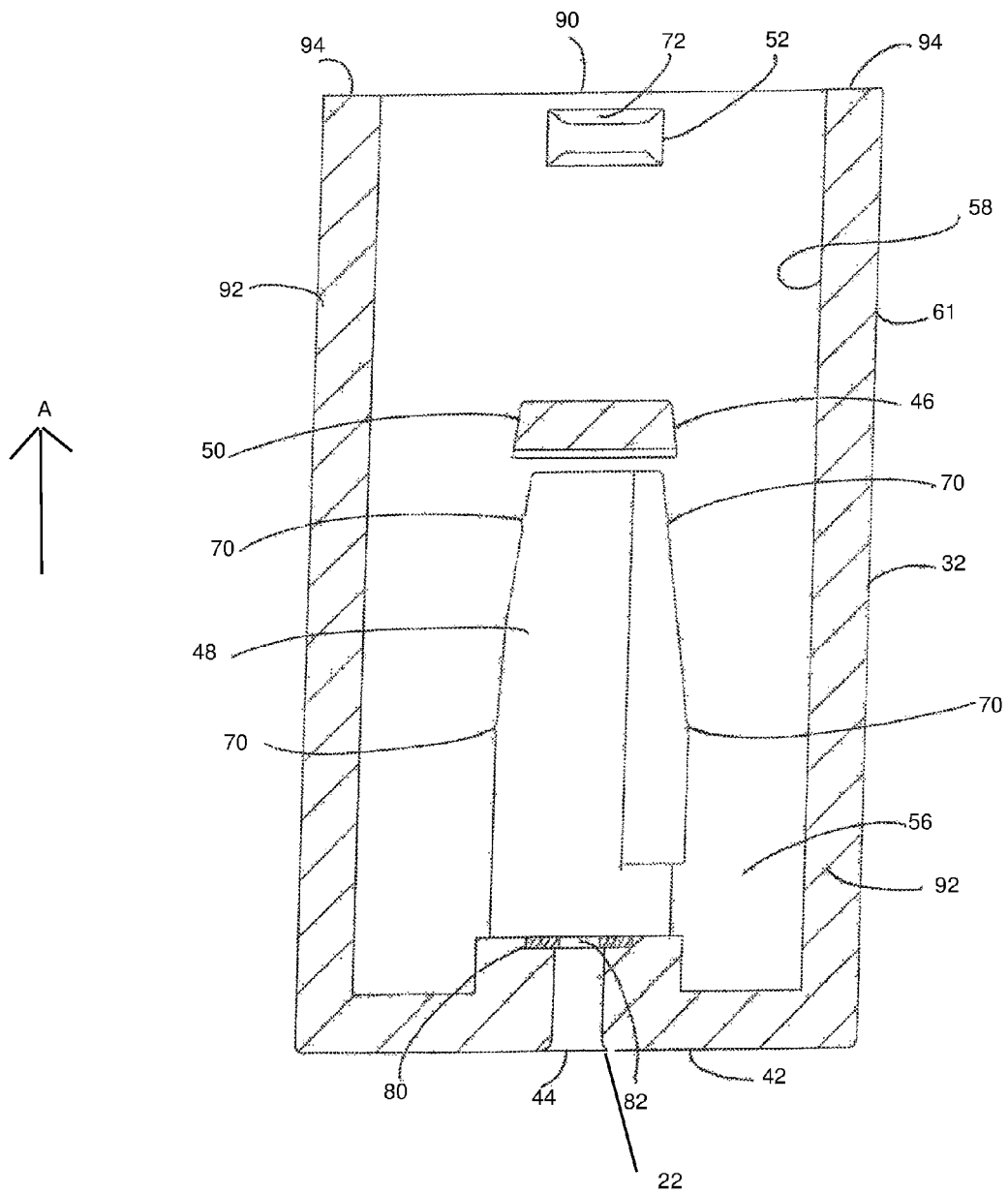
FIG. 5—illustrate sectional illustration of tip protector assembly of FIG. 1 wherein the tension creating element has been omitted for the sake of clarity.
Figure 6A:
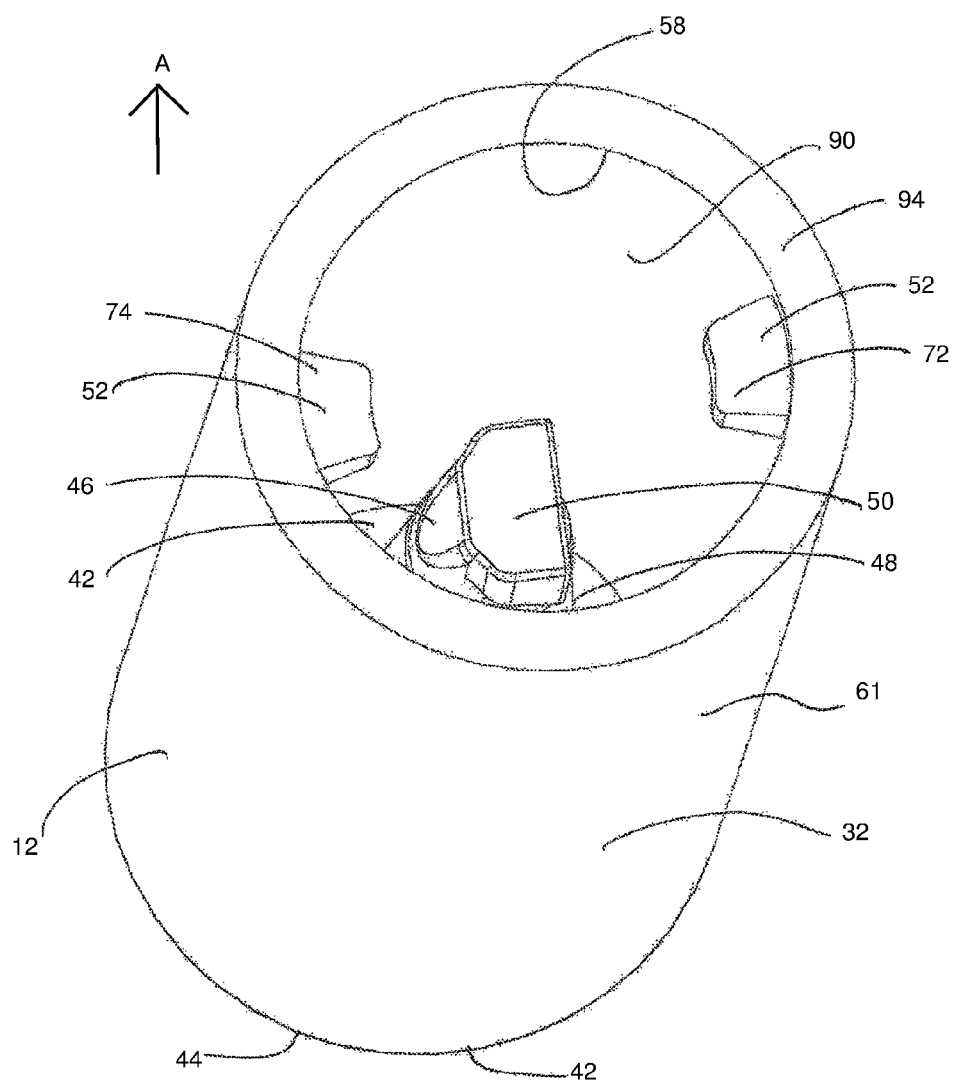
FIGS. 6A-6B illustrate the tip protector assembly of FIG. 1 wherein the tension creating element has been omitted for the sake of clarity.
Figure 6B:
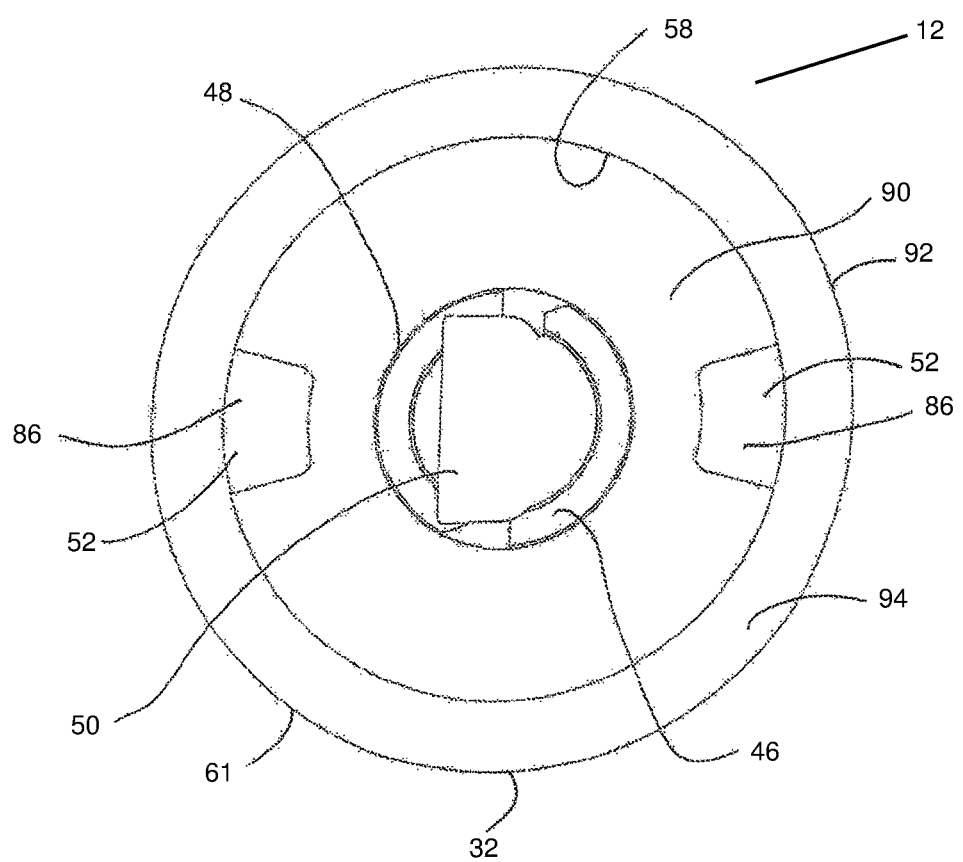

The tip protector assembly 12 is shown with further detail in FIGS. 5, 6A and 6B wherein the tip protector assembly 12 is provided with a base portion 42 having a needle passage 22 extending in the axial direction A from the proximal end 28 of the base portion 42 to a distal side of the base portion 42 with a hollow enclosure 32 formed by the extension of the base portion 42 in a direction generally parallel to the axial direction A wherein the distal end 30 of the hollow enclosure 32 has a substantially circular opening 90 allowing the needle 14 to pass there-through. First 46 and second 48 arms are made integrally within the hollow enclosure 32 and extend from the distal side of the base portion 42 in an axial direction A wherein the region between the first 46 and second 48 arms and the hollow enclosure 32 defines open space 56. First locking means 52 in the form of for example, at least a pair of part-annular locking protrusions 72 in a direction opposing each other are provided to secure the tip protector assembly 12 with the second locking means 54 provided on the catheter hub 24 such that the tip protector assembly 12 secured outside the body of the said catheter hub 24 when the needle 14 is in its ready position. The outer profile of the tip protector assembly 12 in particular the hollow enclosure 32 has a substantially cylindrical shape or a tube like shape. It is to be noted however, that the outer profile of the tip protector assembly 12 need not necessarily be cylindrical in shape or tube like shape and can have any other shape such as a rectangular, square or any other suitable shape.

Figures 7A, 7B, 7C:
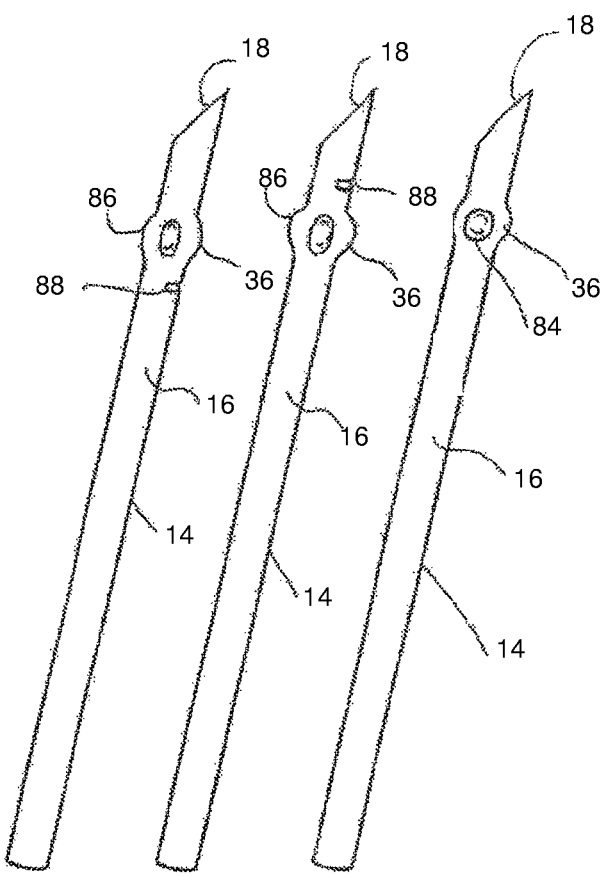
FIG. 7A-7C are illustrations of different embodiments of the needles.
Figure 8:
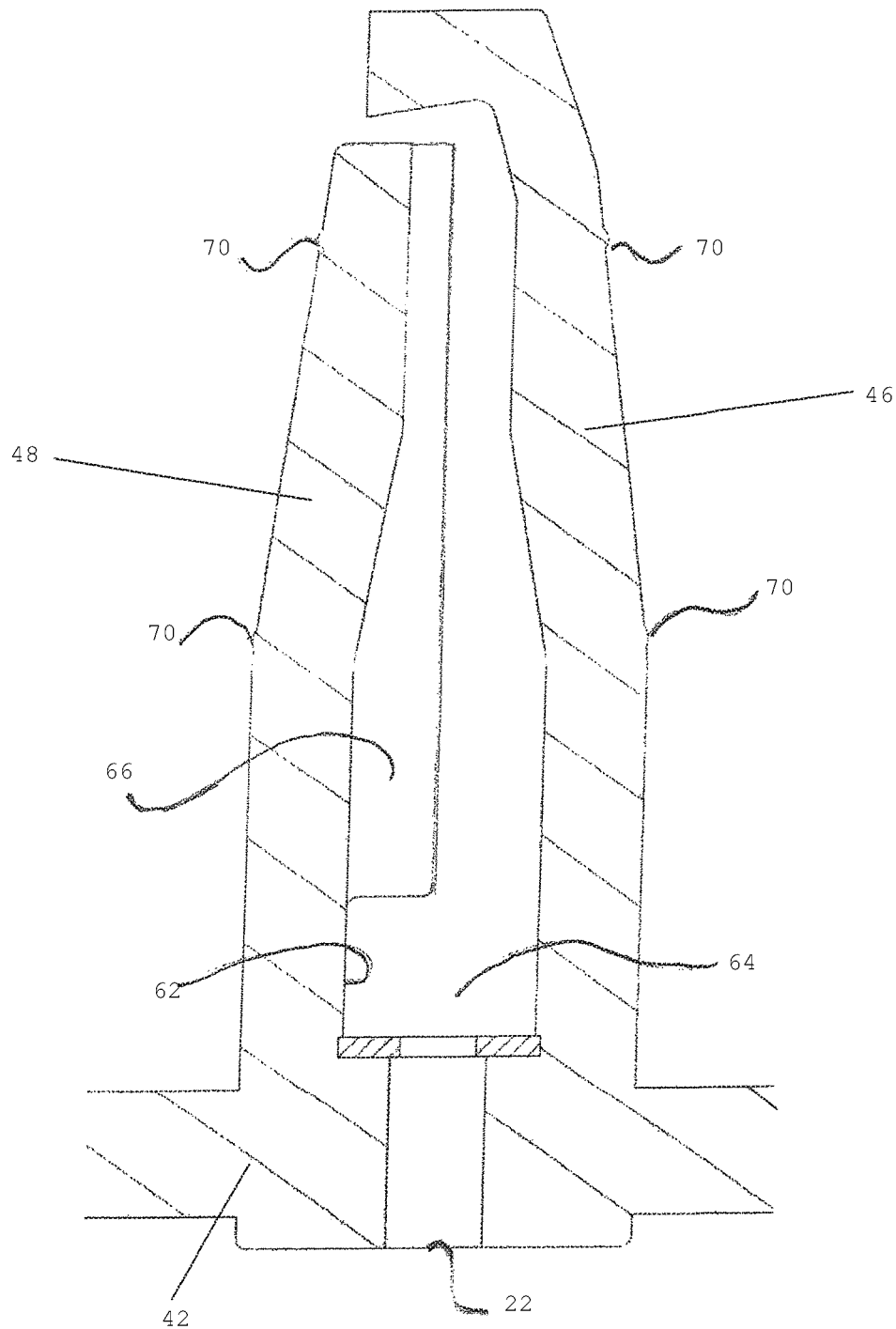
FIG. 8 illustrates the two arms of the tip protector assembly without the tension element.

FIG. 7A shows an embodiment of a needle 14 having a needle shaft 16, a needle tip 18 and a change in profile 34 in the form of an enlargement 36 formed for example, by a crimp. The crimp is made by a local depression 84 such that lateral protrusions 86 result from the crimping process. Preferably, the crimping process is controlled such that the internal cross-sectional area of the needle 14 is not reduced substantially such that the internal profile of the needle shaft 16 is not affected.

FIG. 7B shows the needle 14 according to FIG. 6A, however having a slit forming an opening 88 arranged slightly distally from the change in profile 34, such that it is still arranged within the catheter tube 26 in the ready position. The opening 88 just extends over about 0.5 mm in axial direction A and provides a thorough hole through the needle 14 wall. Thereby, an early blood flashback within the transparent catheter tube 26 can be achieved when the needle 14 is positioned into the patient's vein. Based on this blood flashback, the practitioner can see right after puncturing the patient whether the needle 14 has been positioned correctly due to a small amount of patient's blood oozing out the space between the needle shaft 16 and the transparent catheter shaft.

FIG. 7C shows the needle 14 according to FIG. 7B, however with the slit forming an opening 88 arranged proximally from the change in profile 34. The opening 88 is dimensioned such that it does not affect the functioning of the tip protector assembly 12.

The method of using the IV catheter assembly 10 can be understood whereby the catheter assembly is inserted into a patient by puncturing the skin and the vein therein of the patient with pointed tip of the needle. The needle 14 and catheter tube 26 are introduced into the patient's vein by the healthcare worker. Once the catheter tube 26 is securely within the vein of the patient and a successful flashback is detected, the healthcare worker withdraws the needle 14 from the vein and the catheter tube 26 simultaneously with the catheter securely lodged within the vein of the patient. The needle tip 18 as retracted from the catheter assembly is thereafter automatically secured in the tip protector assembly 12 being entrapped therein.

The IV catheter assembly 10 including tip protector assembly 12 of the invention can be manufactured at reduced costs while at the same time the safety of the IV catheter assembly 10 is increased. The IV catheter assembly 10 including the tip protector assembly 12 is particularly inexpensive to manufacture if the base portion 42, the hollow enclosure 32 and the first 46 and second 48 arms integrally made from a first material. The first material may, for example, be a plastic material. Thus, the base portion 42, the hollow enclosure 32 and the first 46 and second 48 arms could be manufactured by injection molding.

Alternatively, the base portion 42, hollow enclosure 32 and one of the first 46 and second 48 arms could be integrally made from a first material, for example a plastic material and the other one of the first 46 and second 48 arms could be made from a second material different from said first material. For example, said one of the first 46 and second 48 arms could include a strip of material having spring-like properties, e.g. a strip of sheet metal or any other suitable material.

It is to be understood that securing the tip protector assembly 12 outside the catheter hub 24 by means of first 52 and second 54 locking is a simple measure achieving an independent and safe seat of the tip protector assembly 12 and which effectively prevents accidental removal of the tip protector assembly 12 prior to the needle tip 18 being received in the tip protector assembly 12. Not only this arrangement ensures correct protective function of the tip protector assembly 12 but it also removes entirely the problem of pre-mature release faced with the needle 14 safety devices of the prior art when such needle 14 safety devices are retained inside the chamber defined by the catheter hub 24 and when retracting forces applied on the needle 14 while disengaging the needle hub 20 from the catheter hub 24. Hence, in the present invention the risk of premature release of the tip protector assembly 12 during withdrawal of the needle 14 is substantially removed and, thus, the risk of accidental pricking by the needle 14 is reduced.

Thus, the catheter assembly of the present invention provides many advantages over prior art. The tip protector assembly 12 having an outer wall 61 forming a hollow enclosure 32 provides a safe reliable and effective automatic tip protection mechanism when the needle 14 is withdrawn from the catheter as well as a safe, reliable and effecting means and mechanism for engaging the tip protector assembly 12 in a locking arrangement with the catheter hub 24 being secured outside the body of the said catheter hub 24 when the needle 14 is in its ready position.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. For example, the tip protector assembly 12 of the present invention can also be adapted such that without including the stopper element 80. In this case, the outer profile of the enlargement 36 on the needle shaft 16 must be greater than the profile of the thorough-bore 44 provided in the base portion 42 of the tip-protector assembly, in order to prevent the tip protector assembly 12 from sliding off the needle 14 in a distal direction. Thus, from the foregoing description, it will be apparent to one of ordinary skill in the art that many changes and modifications can be made thereto without departing from the spirit or scope of the invention as set forth herein.

Accordingly, it is not intended that the scope of the foregoing description be limited to the exact description set forth above, but rather that such description be construed as encompassing all of the features of patentable novelty that reside in the present invention, including all the features and embodiments that would be treated as equivalents thereof by those skilled in the relevant art. Thus, it is intended that the scope of the present invention herein disclosed should not be limited by the particular disclosed embodiments described above.

IN/PA No. 1217

REFERENCE NUMERALS

10 IV catheter assembly
12 tip protector assembly
14 needle
16 needle shaft
18 needle tip
20 needle hub
22 needle passage
24 catheter hub
26 catheter tube
28 proximal end
30 distal end
32 hollow enclosure
34 change in profile
36 enlargement
38 proximal section
40 distal section
42 base portion
44 thorough bore
46 first arm
48 second arm
50 angled end section
52 first locking means
54 second locking means
56 open space
58 inner wall
60 outer wall
62 internal recess
64 cavity or cut out
66 protective side flap
68 tension creating element
70 tapered outer surface
72 locking protrusion
74 locking depression/grooves/recess
76 locking lug
78 locking thread
80 stopper element
82 axial bore
84 local depression
86 lateral protrusion
88 opening
90 circular opening
92 circular wall
94 peripheral surface
A axial direction

What is claimed is:

1. A safety IV catheter assembly comprising:
a catheter tube having a distal end and a proximal end;
a catheter hub having a distal end and a proximal end;
a needle extending through the catheter hub and the catheter tube having opposite proximal and distal ends defining an axial direction A, wherein the proximal end is joined to a needle hub and the distal end forms a needle tip and a change in profile is provided between the proximal and distal ends of the needle; and
a tip protector assembly being arranged movably on the needle in-between the catheter hub and needle hub, said tip protector including:
  a base portion having a needle passage extending in the axial direction from the proximal end of the base portion to a distal side of the base portion;
  a hollow enclosure integrally formed by the extension of the base portion in a direction generally parallel to the axial direction; wherein the distal end of the hollow enclosure has a substantially circular opening allowing the needle to pass there-through;
  first and second arms of unitary construction with said base portion and provided within the said hollow enclosure, said first and second arms extending from the distal side of the base portion in the axial direction, wherein the region between the first and second arms and the hollow enclosure defines open space;
  at least one tension creating element surrounding partially and/or completely the said first and second arms in a region proximal to the distal ends thereof;

at least one stopper element arranged in the base portion having an axial bore with a dimension adapted to a principal outer profile of said needle; and one or more first locking means to lockingly arrange the tip protector assembly outside the catheter hub in an arrangement engaging with one or more second locking means provided on the catheter hub in its ready position, wherein the first arm is deflected radially outwards by the needle against a restoring force.

2. The IV catheter assembly as claimed in claim 1, wherein the hollow enclosure has an outer profile of a substantially circular wall surrounding the first 46 and second arms of the tip protector assembly.

3. The IV catheter assembly as claimed in claim 1, wherein the distal end of the hollow enclosure has a peripheral surface which acts as a locking surface to engage with at least one or more second locking means provided on the catheter hub when the tip protector assembly is in its ready position.

4. The IV catheter assembly as claimed in claim 1, wherein the hollow enclosure has a substantially cylindrical shape or a tubular shape.

5. The IV catheter assembly as claimed in claim 1, wherein the first locking means include one or more locking protrusions or one or more locking depressions or one or more combinations thereof.

6. The IV catheter assembly as claimed in claim 1, wherein the second locking means include one or more locking protrusions or one or more locking depressions or one or more combinations thereof.

7. The IV catheter assembly as claimed in claim 5, wherein at least one of the first and second locking means are adapted to engage rotatably in at least one direction.

8. The IV catheter assembly as claimed in claim 1, wherein at least one of the second locking means include one or more locking threads or one or more locking lugs or one or more combination thereof.

9. The IV catheter assembly as claimed in claim 1, wherein the first locking means are arranged in the inner wall of the hollow enclosure proximal to the distal end in a direction opposing each other.

10. The IV catheter assembly as claimed in 1, wherein at least one of the second locking means are arranged in the outer wall of the catheter hub close to proximal end thereof in a direction opposing each other.

11. The IV catheter assembly as claimed in claim 1, wherein at least one of the second locking means is arranged at the proximal end of the catheter hub.

12. The IV catheter assembly as claimed in claim 1, wherein at least one side of an inner wall of the first and second arms has an internal recess close to the base portion thereof forming a cavity or cut out.

13. The IV catheter assembly as claimed in claim 12, wherein the extension of the region above the internal recess towards the distal end in the axial direction A forms protective side-flaps in at least one side thereof providing a an enclosure for the needle passing therethrough.

14. The IV catheter assembly as claimed in claim 1, wherein the first arm includes a first free end and the second arm includes a second free end extending generally axially in a distal direction from the base portion.

15. The IV catheter assembly as claimed in claim 14, wherein the first free end extends beyond the second free end and overlaps the second free end by an angled end section.

16. The IV catheter assembly as claimed in claim 15, wherein the length and width of the angled end section are larger than the maximum outer profile of the needle and/or its diameter and adapted to confine the needle tip within a tip holding space.

17. The IV catheter assembly as claimed in claim 1, wherein the change in profile is formed by an enlargement of the radial dimension of the needle in at least one direction as compared with the principal profile of the needle having an outer profile one dimension of which is larger than a maximum dimension of the profile of the through bore.

18. The IV catheter assembly as claimed in claim 17, wherein the enlargement is a crimp or a sleeve or annular sleeve or part annular sleeve or a bulge or a section of the needle with added material or combinations thereof.

19. The IV catheter assembly as claimed in 1, wherein the stopper element is arranged being integrally formed within the base portion such that its axial-bore is in general alignment with the needle passage and is made of a second material different from a first material of the base portion.

20. The IV catheter assembly as claimed in claim 1, wherein the stopper element surrounds the needle and is shaped like a disk or a ring or a washer or a tube.

21. The IV catheter assembly as claimed in claim 1, wherein the stopper element partly surrounds the needle and is a slotted disk, ring or tube.

22. The IV catheter assembly as claimed in claim 19, wherein the stopper element includes an axial bore having a cross-section adapted to the principal profile of the needle but being smaller than the radial dimension of the change in profile.

23. The IV catheter assembly as claimed in claim 1, wherein needle shaft is formed with a slit forming an opening arranged distally or proximally from the change in profile.

24. The IV catheter assembly as claimed in claim 1, wherein the tension creating element has the structure forming a link connecting the said first and second arms and arranged in at least one of the either sides of first and second arms of the tip protector assembly.

* * * * *